United States Patent
Saito

(10) Patent No.: US 9,084,529 B2
(45) Date of Patent: Jul. 21, 2015

(54) ENDOSCOPE SYSTEM, PROCESSOR DEVICE THEREOF, AND METHOD FOR DISPLAYING ENDOSCOPIC VIDEO IMAGE

(71) Applicant: FUJIFILM Corporation, Tokyo (JP)

(72) Inventor: Takaaki Saito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 299 days.

(21) Appl. No.: 13/762,429

(22) Filed: Feb. 8, 2013

(65) Prior Publication Data
US 2013/0235177 A1    Sep. 12, 2013

(30) Foreign Application Priority Data
Mar. 12, 2012    (JP) ................. 2012-054503

(51) Int. Cl.
| | |
|---|---|
| A61B 1/04 | (2006.01) |
| A61B 1/00 | (2006.01) A61B 1/06 |
| (2006.01) | A61B 5/00 |
| (2006.01) | A61B 5/1455 |
| (2006.01) | A61B 1/045 |
| (2006.01) | |

(52) U.S. Cl.
CPC ............ *A61B 1/00009* (2013.01); *A61B 1/045* (2013.01); *A61B 1/0638* (2013.01); *A61B 5/0084* (2013.01); *A61B 5/14551* (2013.01); *A61B 1/0005* (2013.01); *A61B 1/0653* (2013.01)

(58) Field of Classification Search
CPC ......... H04N 7/185; H04N 7/18; H04N 7/183; H04N 2005/2255; A61B 1/05; A61B 1/00096; A61B 1/042; A61B 1/041; A61B 1/00193; A61B 1/00002; A61B 1/00009; A61B 1/00055; A61B 1/0005; A61B 1/045; A61B 1/0638; A61B 5/0084; A61B 5/14551
USPC ........... 348/65, 67, 68, 70, 71, 77, 45, 82, 84, 348/85; 356/241.1, 241.3, 241.4; 359/367; 600/323, 101, 103, 108, 109, 112, 118, 600/160
IPC ............................. A61B 1/04,1/06; H04N 7/18
See application file for complete search history.

(56) References Cited

U.S. PATENT DOCUMENTS

| | | | |
|---|---|---|---|
| 2013/0006109 A1* | 1/2013 | Takei et al. .................... | 600/432 |
| 2013/0113906 A1* | 5/2013 | Saito ............................... | 348/68 |

FOREIGN PATENT DOCUMENTS

| | | |
|---|---|---|
| JP | 61-71791 A | 4/1986 |
| JP | 8-68952 A | 3/1996 |

OTHER PUBLICATIONS

Extended European Search Report, dated Apr. 25, 2013, for European Application No. 13155255.6.
Japanese Office Action dated Jan. 22, 2014 issued in corresponding Japanese Patent Application No. 2012-054503.

* cited by examiner

*Primary Examiner* — Sherrie Hsia
(74) *Attorney, Agent, or Firm* — Birch, Stewart, Kolasch & Birch, LLP

(57) ABSTRACT

In a special mode, a first frame image including a blue signal B1, a green signal G1, and a red signal R1 is captured in a first frame period. In a second frame period, a second frame image including a blue signal B2, a green signal G2, and a red signal R2 is captured. An oxygen saturation level calculator calculates an oxygen saturation level of each pixel based on signal ratios B1/G2 and R2/G2, and sequentially outputs obtained special images on a monitor. Whenever the special image is produced, a signal ratio R2/R1 is calculated. When the signal ratio R2/R1 exceeds a threshold value, a warning sign "!!" is displayed. When the signal ratio R2/R1 is larger than a predetermined range S, a warning sign "HIGH $StO_2$" is displayed. When the signal ratio R2/R1 is smaller than the range S, a warning sign "LOW $StO_2$" is displayed.

13 Claims, 11 Drawing Sheets

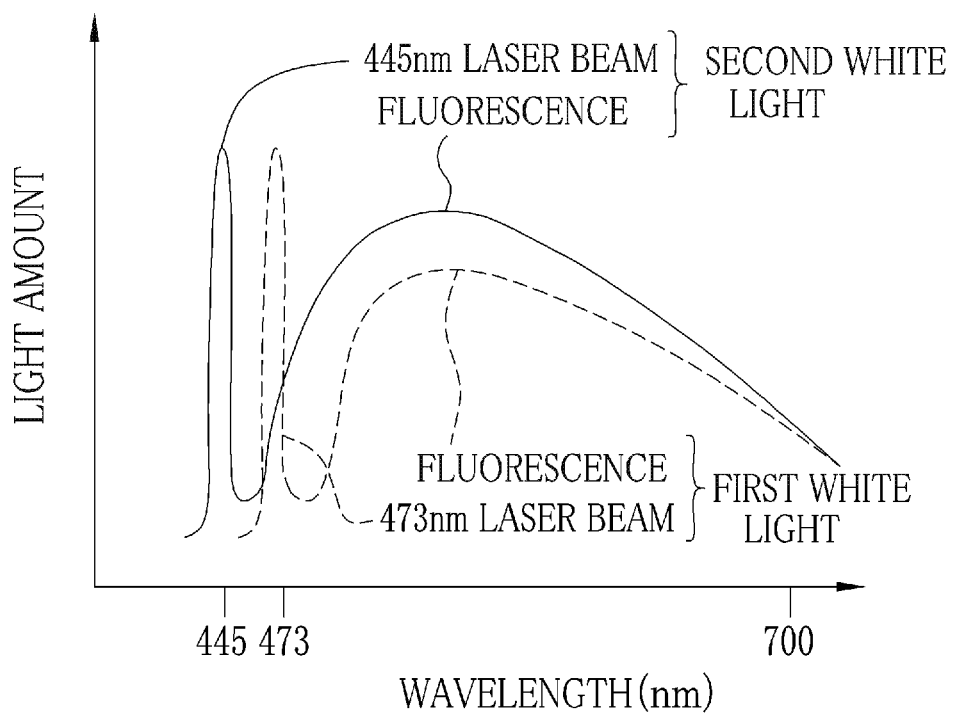

ENDOSCOPE SYSTEM, PROCESSOR DEVICE THEREOF, AND METHOD FOR DISPLAYING ENDOSCOPIC VIDEO IMAGE

BACKGROUND OF THE INVENTION

1. Field of the Invention

The present invention relates to an endoscope system, a processor device thereof, and a method for displaying an endoscopic video image.

2. Description Related to the Prior Art

Endoscopy using an endoscope system is widely employed in a medical field. The endoscope system is constituted of an electronic endoscope, a light source device, a processor device, a monitor, and the like. In recent years, there is known an endoscope system that is provided with not only a normal mode (normal light observation mode) for observing an entire image of the inside of a body cavity under white light having a wide wavelength band, but also a special mode (special light observation mode) for performing observation from various viewpoints using special light in a specific narrow wavelength band.

In the normal mode, normal light such as xenon light in the wide wavelength band is applied to an internal body portion, and a color image sensor captures the light reflected from the body portion. A color video image obtained by the image sensor is displayed on the monitor. In another technique, as described in Japanese Patent Laid-Open Publication No. 08-068952, the normal light is color-separated into three colors of light, and an endoscope system sequentially applies the three colors of light to the internal body portion. A monochrome image sensor captures the light reflected therefrom by a frame sequential method. Three color frame images obtained thereby are merged into a full color video image.

In the special mode, a blood vessel pattern obtaining technique is known in which a blood vessel in a specific depth is enhanced using the special light having a wavelength at which hemoglobin has a high light absorption coefficient. Also, there is known an oxygen saturation level obtaining technique. In this technique, a plurality of types of special light that have different wavelengths including a wavelength at which the light absorption coefficient much differs between oxygenated hemoglobin and deoxygenated hemoglobin are sequentially applied to the internal body portion. The reflected light therefrom is captured by a sequential method to obtain a plurality of frame images. The oxygen saturation level is calculated from the plurality of frame images. The above techniques facilitate finding out a lesion such as cancer that is hard to spot under the normal light.

In the case of capturing the plurality of frame images by the sequential method under irradiation with the plurality of types of special light, each individual frame image is captured at different timing. Thus, if displacement occurs among the frame images due to various movements such as a shake of a head assembly of the electronic endoscope and a body motion, artifact arises in an endoscopic image produced from the frame images. As a measure against the artifact, in the system of the Japanese Patent Laid-Open Publication No. 08-068952, the single endoscopic image, which is produced from the RGB three frame images obtained by the frame sequential method, is displayed in color, if the movement is small. The display is switched into monochrome, if the movement is large so as to cause color deviation in the color display.

In the system of the Japanese Patent Laid-Open Publication No. 08-068952, the switching between the color display and the monochrome display is performed manually by keyboard input. This switching operation is often a burden to a doctor who steering the electronic endoscope. To reduce the burden on the doctor, another hand, for example, a switching assistant is required.

SUMMARY OF THE INVENTION

An object of the present invention is to provide an endoscope system, a processor device thereof, and a method for automatically detecting abnormality e.g. the occurrence of artifact in an endoscopic image and displaying a detection result on a monitor, when displaying the endoscopic image based on a plurality of frame images obtained by a frame sequential method.

To achieve the above and other objects, an endoscope system according to the present invention includes a lighting section, an image pickup section, a video image generator, a monitor, and a warning unit. The lighting section sequentially applies a plurality of types of illumination light having different wavelength bands to an internal body portion. The image pickup section sequentially captures reflected light from the internal body portion to obtain a plurality of frames of image signals corresponding to the types of the illumination light. The video image generator produces an endoscopic image of one video frame based on the plurality of frames of image signals, and sequentially outputs a plurality of produced endoscopic images to produce an endoscopic video image. The endoscopic video image is displayed on the monitor. The warning unit issues a warning, when a signal ratio between at least two of the image signals is out of a predetermined range.

The lighting section preferably emits first illumination light in a first frame period and second illumination light in a second frame period. The first and second illumination light preferably has the same spectral distribution in a specific wavelength range. The image pickup section obtains a first image signal in the first frame period and a second image signal in the second frame period, with use of a color image sensor having a specific pixel having a color filter for passing light in the specific wavelength range. When a signal ratio between a first signal component of the first image signal and a second signal component of the second image signal is out of a predetermined range, the warning unit issues the warning. The first signal component refers to a component of the first image signal outputted from the specific pixel. The second signal component refers to a component of the second image signal outputted from the specific pixel.

The first illumination light preferably includes first blue light in a narrow wavelength band and first green to red light in a wide wavelength band. The first green to red light is obtained by wavelength conversion of the first blue light using a wavelength conversion element. The second illumination light preferably includes second blue light in a narrow wavelength band and second green to red light in a wide wavelength band. The second green to red light is obtained by the wavelength conversion of the second blue light using the wavelength conversion element. The wavelength of the first blue light is different from the wavelength of the second blue light. The first and second illumination light preferably has the same spectral distribution in a red wavelength range.

The first and second blue light is preferably emitted from semiconductor light sources.

When the signal ratio is out of a first numerical range, the warning unit preferably issues a first warning about a body motion of the internal body portion or a shake of the image sensor.

The endoscopic video image is preferably an oxygen saturation video image that images an oxygen saturation level of blood. When the signal ratio is out of a second numerical range, the warning unit preferably issues a second warning about the oxygen saturation level.

The warning unit may issue the warning by changing how to display the endoscopic video image on the monitor. The warning unit may issue the warning by displaying a warning sign on the monitor. The warning sign is displayed on the monitor together with the endoscopic video image.

The endoscope system may further include a still image recording section for storing one or more video frames of the endoscopic images as still images in a still image memory, when the signal ratio is within the predetermined range.

A processor device of the endoscope system includes a video image generator and a warning unit. The video image generator produces an endoscopic image of one video frame based on a plurality of frames of image signals, and sequentially outputs a plurality of produced endoscopic images to a monitor to produce an endoscopic video image. The warning unit issues a warning, when a signal ratio between at least two of the image signals is out of a predetermined range.

A method for displaying an endoscopic video image includes the steps of sequentially applying a plurality of types of illumination light having different wavelength bands to an internal body portion; sequentially capturing reflected light from the internal body portion to obtain a plurality of frames of image signals corresponding to the types of illumination light; producing an endoscopic image of one video frame based on the plurality of frames of image signals; sequentially displaying on a monitor as an endoscopic video image a plurality of the endoscopic images produced by repetition of the applying step, the capturing step, and the producing step; comparing a signal ratio between at least two of the image signals with a predetermined range; and issuing a warning, when the signal ratio is out of the predetermined range.

According to the present invention, the use of the signal ratio between the image signals, which have correlation with the body motion of the internal body portion and the like, allows automatic detection of the abnormality e.g. the occurrence of the artifact. Furthermore, the detected abnormality is displayed as a warning in the endoscopic video image.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 3 is a graph showing emission spectra of first and second white light;

DESCRIPTION OF THE PREFERRED EMBODIMENTS

Figure 1:
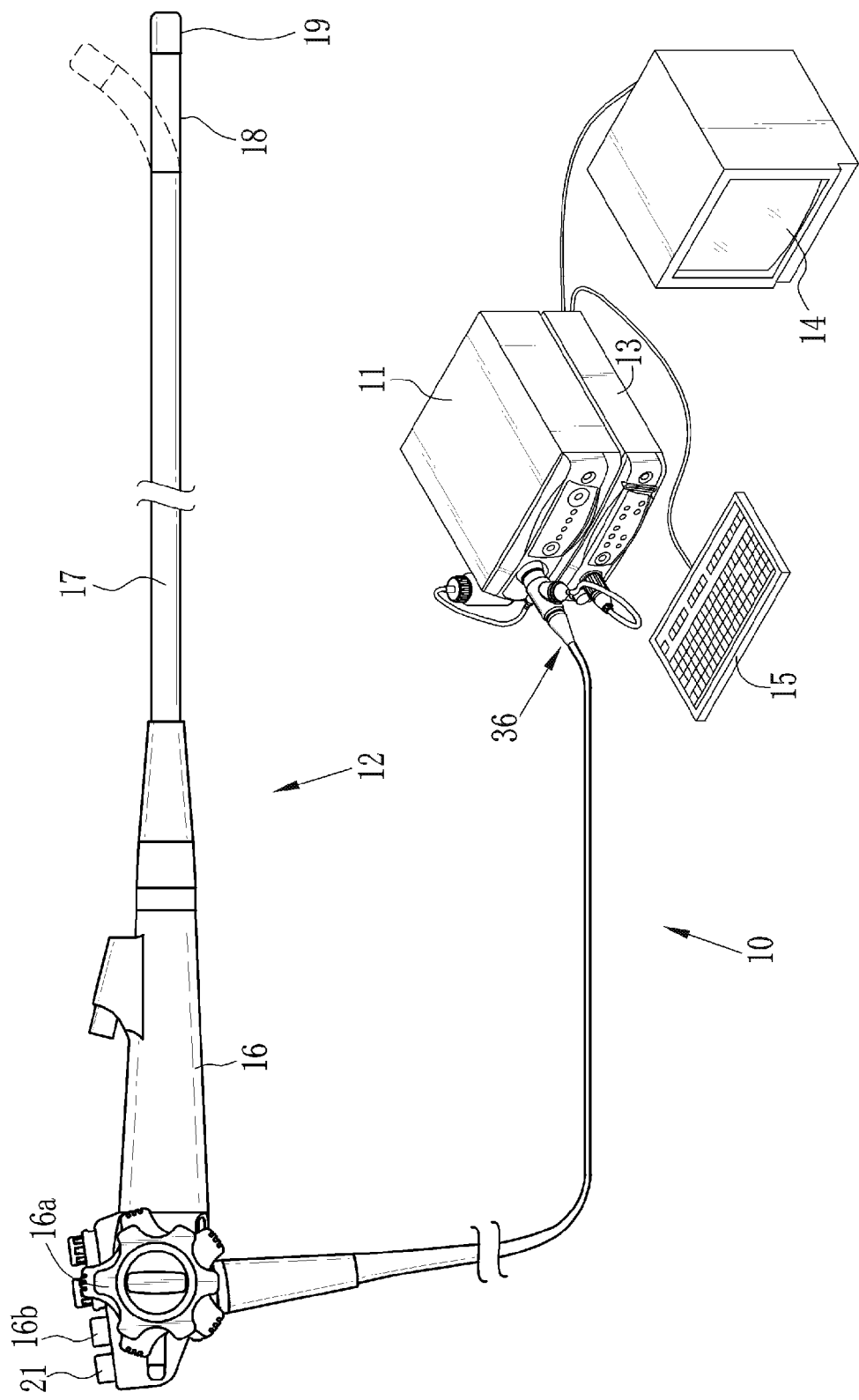
FIG. 1 is an overview of an endoscope system.

As shown in FIG. 1, an endoscope system 10 is constituted of a light source device 11, an electronic endoscope 12, a processor device 13, a monitor 14, and an input device 15 such as a keyboard. The light source device 11 produces a plurality of types of illumination light in specific wavelength bands. The illumination light from the light source device 11 is applied to the inside of a body cavity, and the electronic endoscope 12 images the light reflected therefrom. The processor device 13 produces an endoscopic image from image signals obtained by the electronic endoscope 12. The obtained endoscopic image is displayed on the monitor 14.

The electronic endoscope 12 is provided with a flexible elongated tube 17, a steering assembly 18, and a head assembly 19 disposed in this order from the side of a control handle unit 16. The steering assembly 18 is flexibly bent by a turn of an angle knob 16a provided on the control handle unit 16. By bending the steering assembly 18 in an arbitrary direction and angle, the head assembly 19 is aimed at a desired internal body portion to be examined. The flexible elongated tube 17, the steering assembly 18, and the head assembly 19 are collectively called an insert section.

The endoscope system 10 is switched between a normal mode and a special mode. In the normal mode, a normal video image is produced in the visible region extending from blue to red. In the special mode, a special video image is produced to represent an oxygen saturation level of hemoglobin. The switching is appropriately performed based on input from a mode switch 21 of the electronic endoscope 12 or the input device 15.

Figure 2:
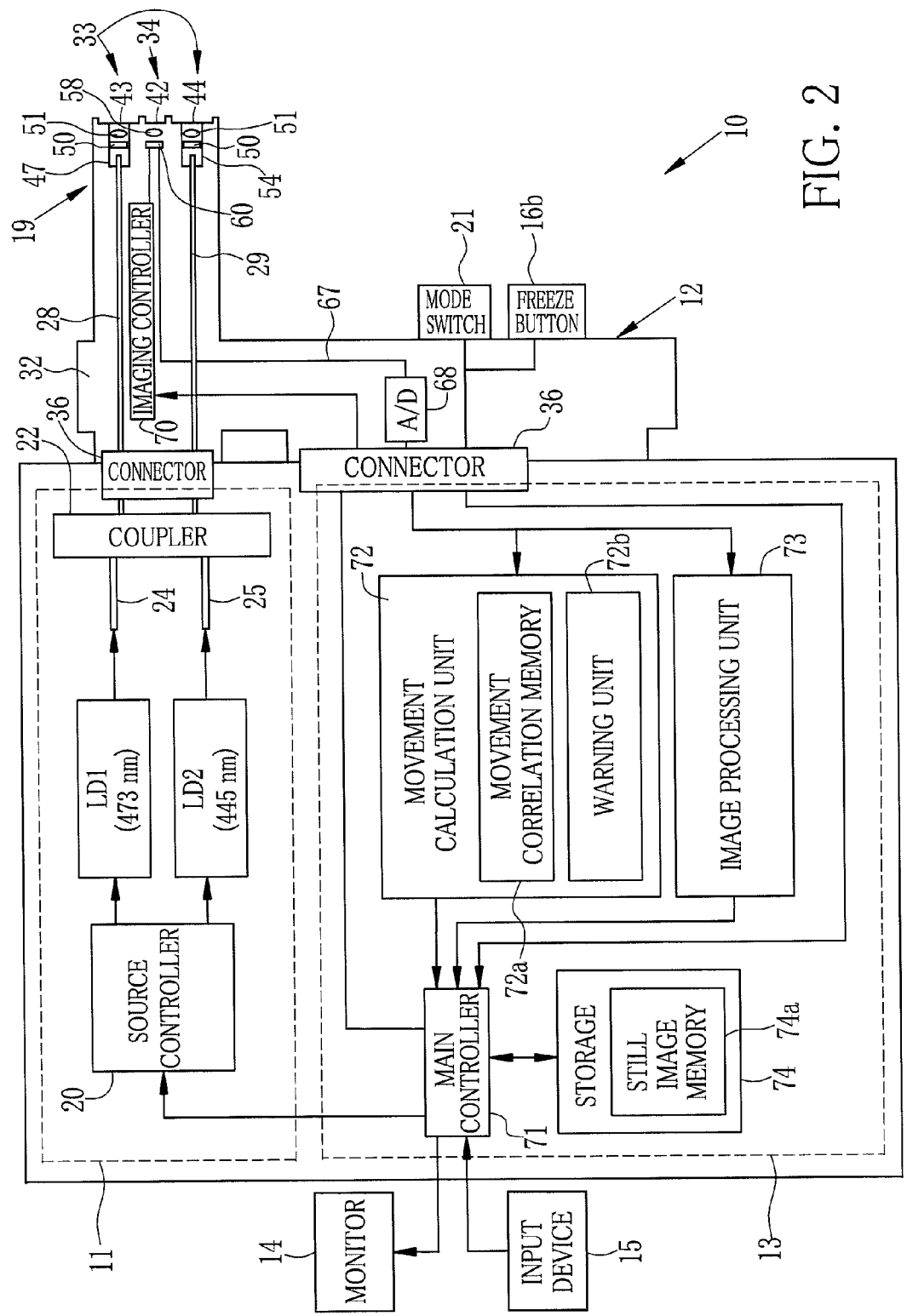
FIG. 2 is a block diagram of the endoscope system.

As shown in FIG. 2, the light source device 11 includes two types of laser sources LD1 and LD2 and a source controller 20. The laser source LD1 emits a first laser beam having a center wavelength of 473 nm. The first laser beam excites a phosphor 50 provided in the head assembly 19, and produces first white light (pseudo white light). The laser source LD2 emits a second laser beam having a center wavelength of 445 nm. The second laser beam excites the phosphor 50, and produces second white light (pseudo white light). Note that, the first laser beam is preferably in a wavelength range of 460 to 480 nm, and the second laser beam is preferably in a wavelength range of 440 to 460 nm.

The first laser beam emitted from the laser source LD1 is incident upon an optical fiber 24 through a condenser lens (not shown). The second laser beam emitted from the laser source LD2 is incident upon an optical fiber 25 through a condenser lens (not shown). As the laser sources LD1 and LD2, a broad-area type InGaN laser diode, InGaNAs laser diode, GaNAs laser diode, or the like is available.

The source controller 20 controls the laser sources LD1 and LD2, and adjusts emission timing of the laser sources LD1 and LD2. In this embodiment, the laser source LD2 is turned on and the laser source LD1 is turned off in the normal mode. In the special mode, the laser sources LD1 and LD2 are alternately turned on and off on a frame-by-frame basis. More specifically, when the laser source LD1 is turned on, the laser source LD2 is turned off. When the laser source LD1 is turned off, the laser source LD2 is turned on.

A coupler 22 branches the first laser beam from the optical fiber 24 in two beams, and enters the branched two beams into light guides 28 and 29, respectively. The coupler 22 also branches the second laser beam from the optical fiber 25 in two beams, and enters the branched two beams into the light guides 28 and 29. Each light guide 28, 29 is made of a fiber bundle into which a number of optical fibers are bound.

The electronic endoscope 12 is provided with a lighting section 33 for applying the two beams transmitted through the light guides 28 and 29 to the internal body portion, and an image pickup section 34 for imaging the internal body portion. The electronic endoscope 12 is also provided with a connector 36 that detachably connects the electronic endoscope 12 to the light source device 11 and the processor device 13.

The lighting section 33 includes two lighting windows 43 and 44 disposed on both right and left sides of the image pickup section 34, and light projection units 47 and 54 disposed in the recess of the lighting windows 43 and 44, respectively. Through the lighting windows 43 and 44, the first or second white light is applied to the internal body portion. Each light projection unit 47, 54 contains the phosphor 50 and a lens 51. The image pickup section 34 includes an imaging window 42, which is disposed approximately at the center of the head assembly 19 to receive light reflected from the internal body portion, and an image sensor 60 disposed in the recess of the imaging window 42.

The phosphor 50 is made of a plurality of types of fluorescent substances (for example, YAG-based fluorescent substance or BAM (BaMgAl$_{10}$O$_{17}$)-based fluorescent substance) that absorb a part of the first laser beam from the laser source LD1 or the second laser beam from the laser source LD2 and emit green to red fluorescence. The entrance of the first or second laser beam into the phosphor 50 produces the pseudo white light, by mixing of the green to red fluorescence emitted from the phosphor 50 and the first or second laser beam passed through the phosphor 50 without being absorbed.

The phosphor 50 preferably has an approximately rectangular parallelepiped shape. The phosphor 50 may be formed by compacting the fluorescent substances by a binder into the rectangular parallelepiped shape. The mixture of the fluorescent substances and resin such as inorganic glass may be formed into the rectangular parallelepiped shape. This phosphor 50 is known under the trademark of Micro White (MW).

As shown in FIG. 3, the first white light, which is produced by entrance of the first laser beam, has a wavelength of 473 nm being a wavelength band of the first laser beam and wavelengths between 480 nm and 700 nm being a wavelength band of the fluorescence excited by the first laser beam. The second white light, which is produced by entrance of the second laser beam, has a wavelength of 445 nm being a wavelength band of the second laser beam and wavelengths between 460 nm and 700 nm being a wavelength band of the fluorescence excited by the second laser beam.

Note that, the white light does not necessarily contain each and every wavelength component of the visible light, as long as it contains a plurality of wavelength components of R(red), G(green), and B(blue) being primary colors, such as the pseudo white light described above. In a broad sense, the white light includes, for example, light having a wavelength component from green to red, light having a wavelength component from blue to green, and the like.

An objective lens 58 is provided in the recess of the imaging window 42 to capture image light of the internal body portion. In the recess of the objective lens 58, the image sensor 60 e.g. a CCD (charged coupled device) image sensor or a CMOS (complementary metal-oxide semiconductor) image sensor is provided to perform photoelectric conversion of the image light.

Figure 4A:
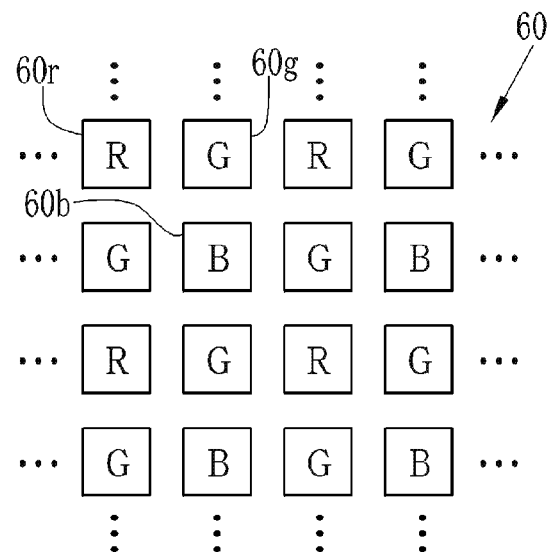
FIG. 4A is an explanatory view showing an arrangement of B pixels, G pixels, and R pixels in a color image sensor.
Figure 4B:
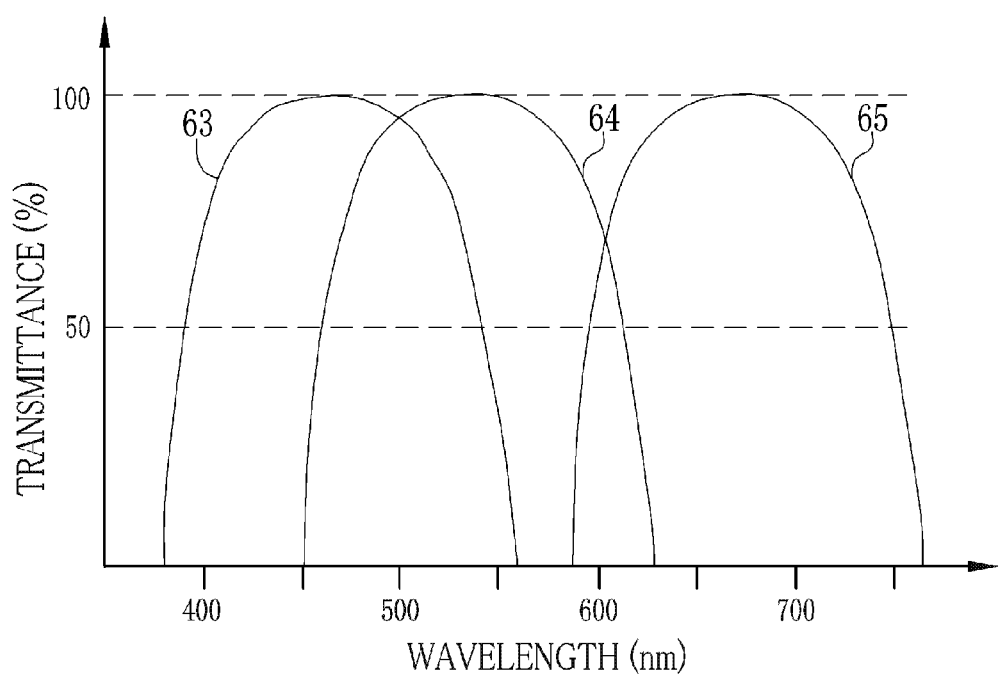
FIG. 4B is a graph showing spectral transmittance of the B pixel, the G pixel, and the R pixel.

The image sensor 60 receives the image light from the objective lens 58 at its light receiving surface (imaging surface), and performs the photoelectric conversion of the received image light to output an analog image signal. In this embodiment, a color CCD is employed as the image sensor 60. As shown in FIG. 4A, the image sensor 60 has arrangement patterns of 2- by 2-pixel arranged in both horizontal and vertical directions in its light receiving surface. Each arrangement pattern includes one B pixel 60$b$ having a B (blue) color filter, two G pixels 60$g$ having a G (green) color filter, and one R pixel 60$r$ having a R (red) color filter. The B, G, and R color filters have high spectral transmittance in a blue wavelength range, a green wavelength range, and a red wavelength range, as represented by curves 63, 64, and 65 of FIG. 4B, respectively.

The analog image signal outputted from the image sensor 60 is inputted to an A/D converter 68 through a cable 67. The A/D converter 68 converts the image signal into a digital image signal in accordance with its voltage level. The converted image signal is inputted to the processor device 13 through the connector 36.

Figure 5A:
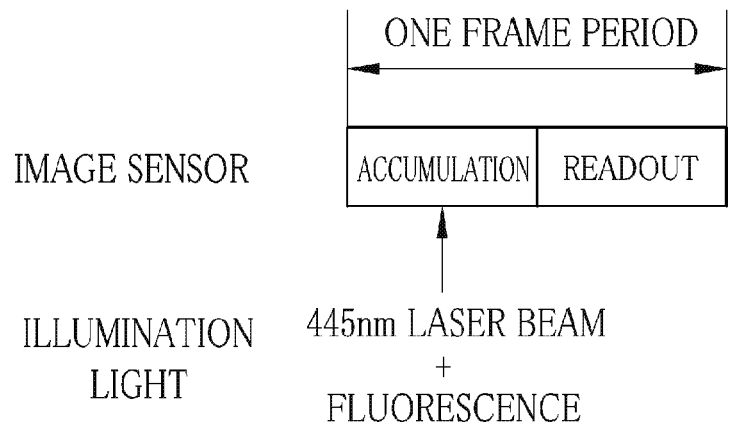
FIG. 5A is an explanatory view of imaging control of an image sensor in a normal mode.

An imaging controller 70 controls the image sensor 60. As shown in FIG. 5A, in the normal mode, electric charge produced by the second white light (445 nm+fluorescence) is accumulated and read out within one frame period. This accumulation and readout are repeated while the endoscope system 10 stays in the normal mode.

Figure 5B:
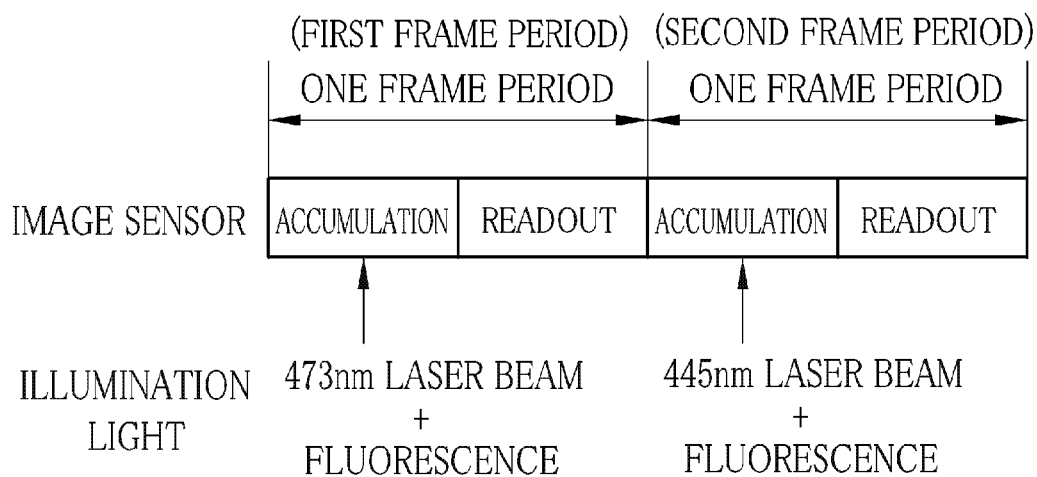
FIG. 5B is an explanatory view of imaging control of the image sensor in a special mode.

In the special mode, on the other hand, as shown in FIG. 5B, electric charge produced by the first white light (473 nm+fluorescence) is accumulated and read out in a first frame period. After that, the electric charge produced by the second white light is accumulated and read out in a second frame period. The first and second frame periods are alternately repeated while the endoscope system 10 stays in the special mode.

In the special mode, B1 represents a blue signal outputted from the B pixels of the image sensor 60 in the first frame period. G1 represents a green signal outputted from the G pixels, and R1 represents a red signal outputted from the R pixels in the first frame period. B2 represents a blue signal outputted from the B pixels in the second frame period. G2 represents a green signal outputted from the G pixels, and R2 represents a red signal outputted from the R pixels in the second frame period.

The processor device 13 is constituted of a main controller 71, a movement calculation unit 72, an image processing unit 73, and storage 74. The main controller 71 is connected to the monitor 14 and the input device 15. The main controller 71 controls the operation of the image processing unit 73, the source controller 20 of the light source device 11, the imaging controller 70 of the electronic endoscope 12, and the monitor 14 based on input from the mode switch 21 of the electronic endoscope 12 and the input device 15.

The movement calculation unit 72 calculates a signal ratio R2/R1 between the red signal R1 of a first frame image obtained in the first frame period and the red signal R2 of a second frame image obtained in the second frame period. Then, the movement calculation unit 72 calculates from the signal ratio R2/R1 a movement M, which represents in numerical form various movements including a shake of the head assembly 19 and a body motion of the internal body portion. The correlation between the movement M and the signal ratio R2/R1 is stored in a movement correlation memory 72*a*.

Figure 6A:
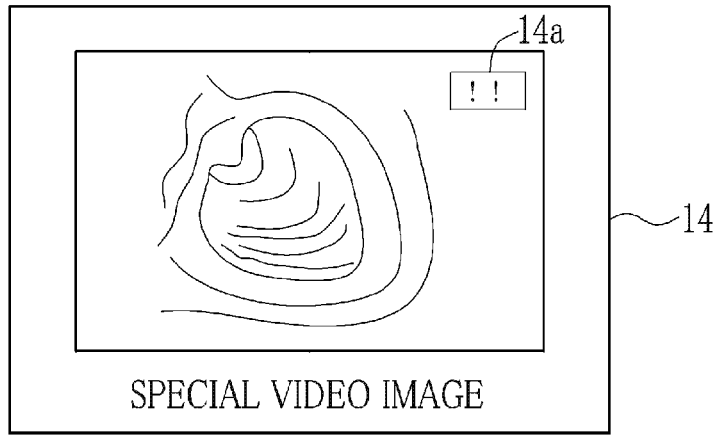
FIG. 6A is an explanatory view of a special video image on which a warning about artifact is displayed.

When the movement M is a predetermined threshold value or more, artifact tends to occur due to the various movements. Therefore, as shown in FIG. 6A, a warning unit 72*b* puts in the special video image a warning sign "!!", which indicates "there is a possibility of the occurrence of artifact". The movement M calculated by the movement calculation unit 72 is sent to the image processing unit 73. Note that, the artifact can occur not only by the movements but also by variation in the intensity ratio between the first and second white light caused by exposure control. For this reason, the intensity ratio between the first and second white light is preferably kept constant.

The reason why the movement M is calculated from the signal ratio R2/R1, as described above, is as follows. In the special mode, the first white light emitted in the first frame period and the second white light emitted in the second frame period have approximately the same spectral distribution in the red wavelength range (see FIG. 3). Thus, if no movement occurs, the signal ratio R2/R1 between the red signals R2 and R1 stays at an almost constant value C, which depends on the intensity ratio between the first and second white light. On the contrary, if any movement occurs, the signal ratio R2/R1 deviates from the constant value C in accordance with the amount of the movement. For this reason, the movement M is obtainable by calculating a deviation of the signal ratio R2/R1 from the constant value C.

Figure 6B:
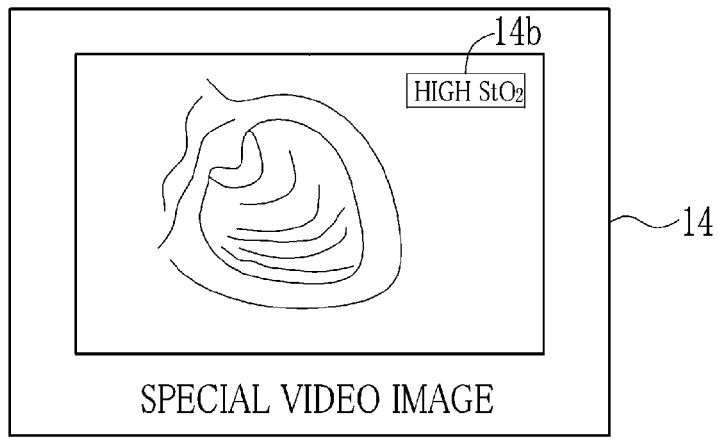
FIG. 6B is an explanatory view of the special video image on which a warning about an oxygen saturation level is displayed.
Figure 6C:
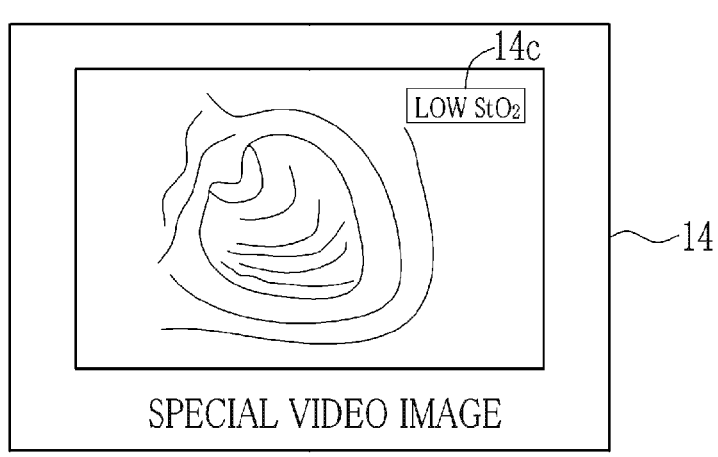
FIG. 6C is an explanatory view of the special video image on which another warning about the oxygen saturation level is displayed.

When the signal ratio R2/R1 calculated by the movement calculation unit 72 is out of a predetermined range S, the warning unit 72*b* puts in the special video image a warning sign for indicating that there is a possibility of the occurrence of an error in calculation of the oxygen saturation level. For example, when the signal ratio R2/R1 is larger than the predetermined range S, as shown in FIG. 6B, a warning sign "HIGH StO$_2$" 14*b* is put in the special video image to indicate that "a calculated oxygen saturation level is possibly higher than an actual value". On the other hand, when the signal ratio R2/R1 is smaller than the predetermined range S, as shown in FIG. 6C, a warning sign "LOW StO$_2$" 14*c* is put in the special video image to indicate that "a calculated oxygen saturation level is possibly lower than an actual value". Note that, the warning signs about the oxygen saturation level and the artifact may be displayed at the same time on the monitor 14.

The reason why the error in calculation of the oxygen saturation level varies depending on the signal ratio R2/R1 is as follows. In the special mode, when the head assembly 19 gets near to the internal body portion, the size of an object becomes larger in the second frame image than that in the first frame image due to optical properties of the objective lens 58. In other words, the distance between the head assembly 19 and the object is shorter in the second frame image, so the amount of light exposure is larger in the second frame image than that in the first frame image. In this case, since the signal ratio R2/R1 becomes larger than the predetermined range S, the oxygen saturation level (correlates with B1/G2) tends to be larger than the actual value.

On the contrary, when the head assembly 19 is moved away from the internal body portion, the distance between the head assembly 19 and the object is shorter in the first frame image, so the amount of light exposure is larger in the first frame image than that in the second frame image. In this case, since the signal ratio R2/R1 becomes smaller than the predetermined range S, so the oxygen saturation level tends to be smaller than the actual value.

Figure 7:
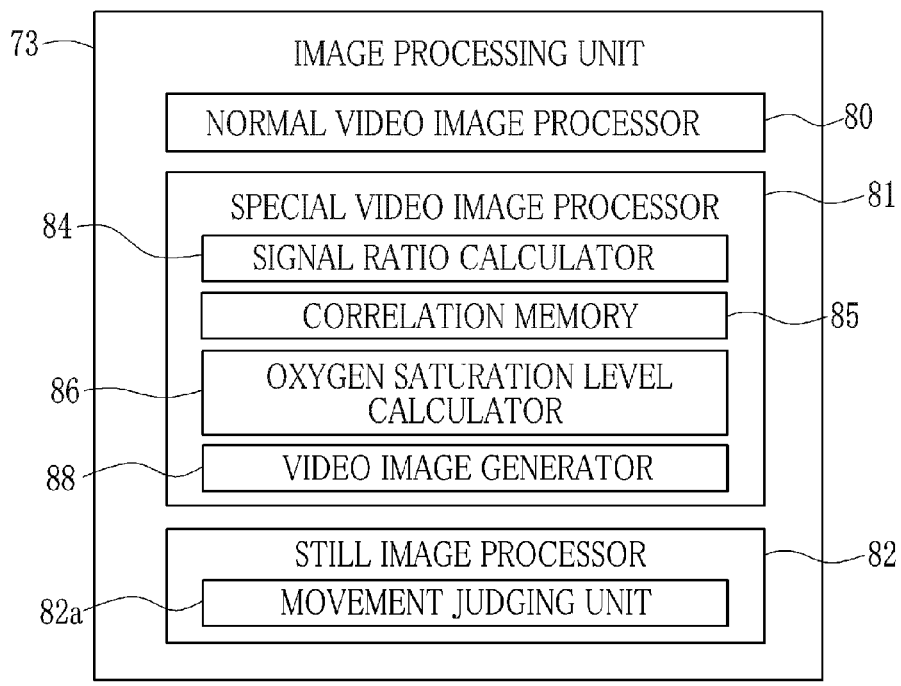
FIG. 7 is a block diagram of an image processing unit.

As shown in FIG. 7, the image processing unit 73 includes a normal video image processor 80, a special video image processor 81, and a still image processor 82. The image processing unit 73 applies predetermined image processing to the image signal from the electronic endoscope 12. The normal video image processor 80 applies the predetermined image processing to the image signal obtained in the normal mode to produce a normal video image.

The special video image processor 81 calculates the oxygen saturation level of blood based on the image signal obtained in the special mode, and produces a special video image (oxygen saturation video image) in which the normal video image is artificially colored. The special video image processor 81 includes a signal ratio calculator 84, a correlation memory 85, an oxygen saturation level calculator 86, and a video image generator 88.

The signal ratio calculator 84 calculates a signal ratio B1/G2 between the blue signal B1 of the first frame image and the green signal G2 of the second frame image, and a signal ratio R2/G2 between the red signal R2 of the second frame image and the green signal G2 of the second frame image. The signal ratio calculator 84 calculates the signal ratios with respect to the pixel situated in the same position. The signal ratios may be calculated with respect to each and every pixel, or only in pixels situated within a blood vessel area. In this case, the blood vessel area is determined based on difference in the image signal between the blood vessel area and the other area.

Figure 8:
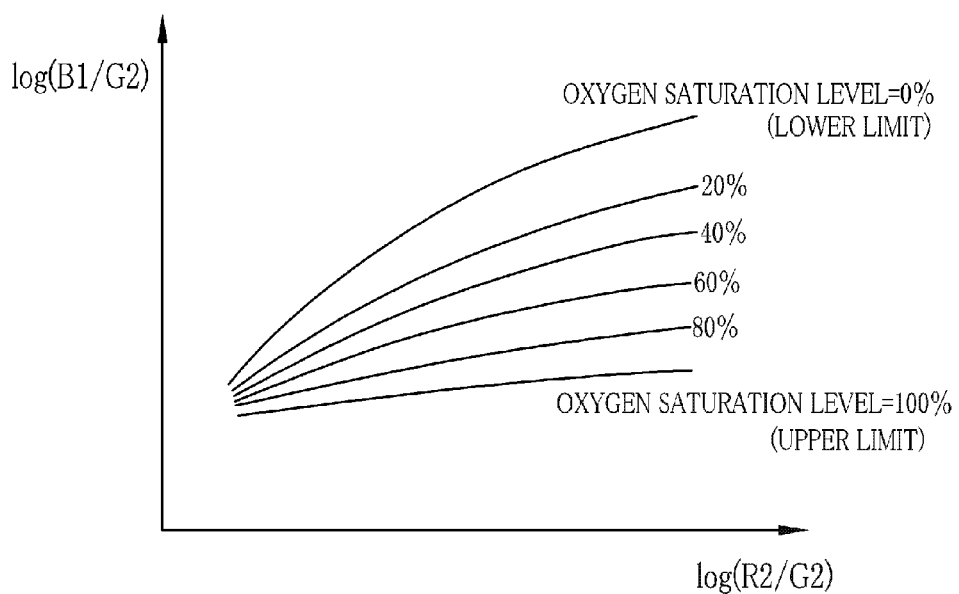
FIG. 8 is a graph showing the correlation among the oxygen saturation level and signal ratios B1/G2 and R2/G2.

The correlation memory 85 stores the correlation among the signal ratios B1/G2 and R2/G2 and the oxygen saturation level. As shown in FIG. 8, this correlation takes the form of a two-dimensional table in which contour lines representing the oxygen saturation level are defined in two-dimensional space. The position and shape of the contour lines are obtained by physical simulation of light scattering, and are variable in accordance with blood volume. For example, variation in the blood volume widens or narrows distance between the contour lines. Note that, the signal ratios B1/G2 and R2/G2 are depicted in log scale.

Figure 9:
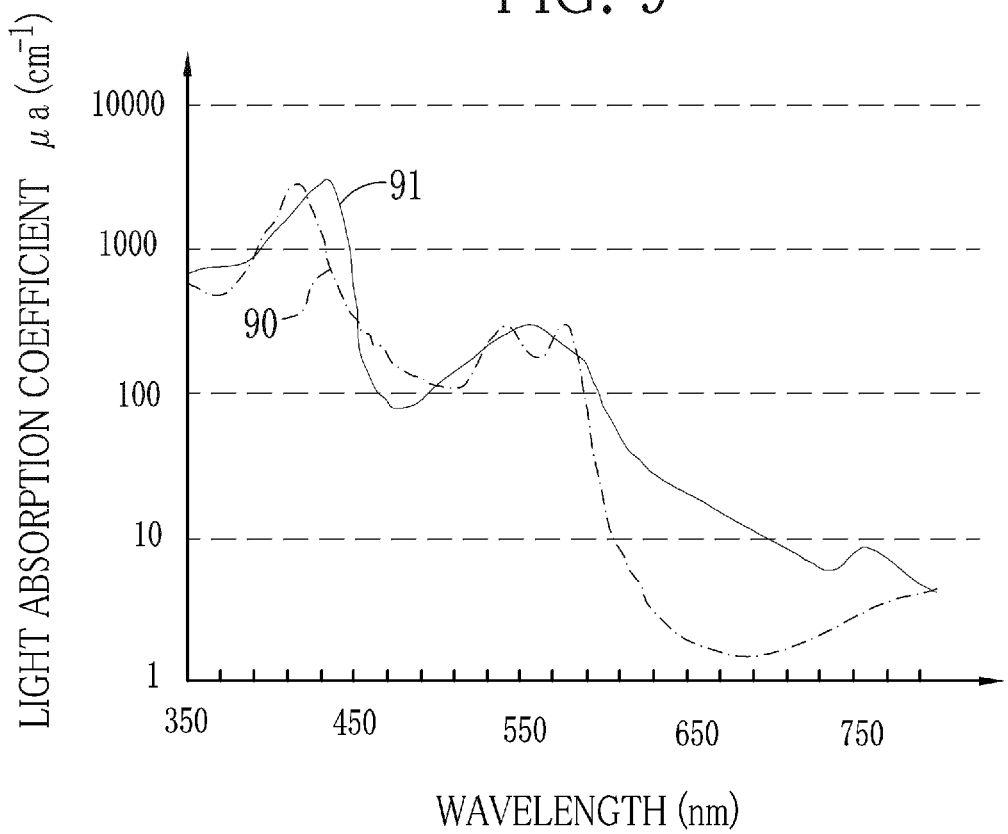
FIG. 9 is a graph showing a light absorption coefficient of oxygenated hemoglobin and deoxygenated hemoglobin.

The correlation is closely related to the light absorbing property and light scattering property of oxygenated hemoglobin and deoxygenated hemoglobin, as shown in FIG. 9. In FIG. 9, a line 90 represents a light absorption coefficient of the oxygenated hemoglobin, and a line 91 represents a light absorption coefficient of the deoxygenated hemoglobin. The use of a wavelength of, for example, 473 nm at which the light absorption coefficient much differs between the oxygenated hemoglobin and the deoxygenated hemoglobin allows the obtainment of the oxygen saturation level. However, the blue signal B1 that corresponds to the light of 473 nm is highly dependent not only on the oxygen saturation level but also on the blood volume. Therefore, the use of the signal ratios B1/G2 and R2/G2, which are obtained from the red signal R2 that is mainly dependent on the blood volume and the green signal G2 being a reference signal (standardization signal) of the blue signal B1 and the red signal R2, in addition to the blue signal B1, allows the obtainment of the oxygen saturation level with high accuracy while eliminating the influence of the blood volume.

Figure 10:
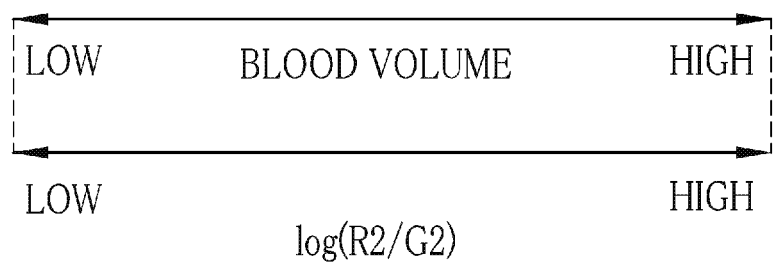
FIG. 10 is a graph showing the correlation between blood volume and the signal ratio R2/G2.

The correlation memory 85 also stores the correlation between the signal ratio R2/G2 and the blood volume as shown in FIG. 10. This correlation takes the form of a one-dimensional table in which the blood volume is increased with increase in the signal ratio R2/G2. The correlation between the signal ratio R2/G2 and the blood volume is used in calculation of the blood volume.

The following three items hold true according to the dependence of the light absorption coefficient on a wavelength:
(1) In the vicinity of a wavelength of 470 nm (for example, the blue wavelength range having a center wavelength of 470 nm±10 nm), the light absorption coefficient largely varies in accordance with difference in the oxygen saturation level.
(2) In the green wavelength range between 540 and 580 nm, a mean value of the light absorption coefficient is insusceptible to the oxygen saturation level.
(3) In the red wavelength range between 590 and 700 nm, the light absorption coefficient seems to vary largely in accordance with the oxygen saturation level, but in actual fact, is insusceptible to the oxygen saturation level because a value of the light absorption coefficient is very small.

The reason why the signal ratio B1/G2 increases with increase in the signal ratio R2/G2, in other words, why the contour line representing the oxygen saturation level of 0% ascends slantly, as shown in FIG. 8, is as follows. As described above, the blood volume increases with increase in the signal ratio R2/G2, because of the correlation between the signal ratio R2/G2 and the blood volume. Out of the signals B1, G2, and R2, a signal value of the green signal G2 decreases most greatly with increase in the blood volume, and a signal value of the blue signal B1 decreases next greatly. This is because the light absorption coefficient is higher at a wavelength range of 540 to 580 nm included in the green signal G2 than that at a wavelength range of around 470 nm included in the blue signal B1 (see FIG. 9). Thus, as for the signal ratio B1/G2, the signal value of the green signal G2 decreases more greatly than the signal value of the blue signal B1 with increase in the blood volume. In other words, the signal ratio B1/G2 increases with increase in the blood volume.

Figure 11:
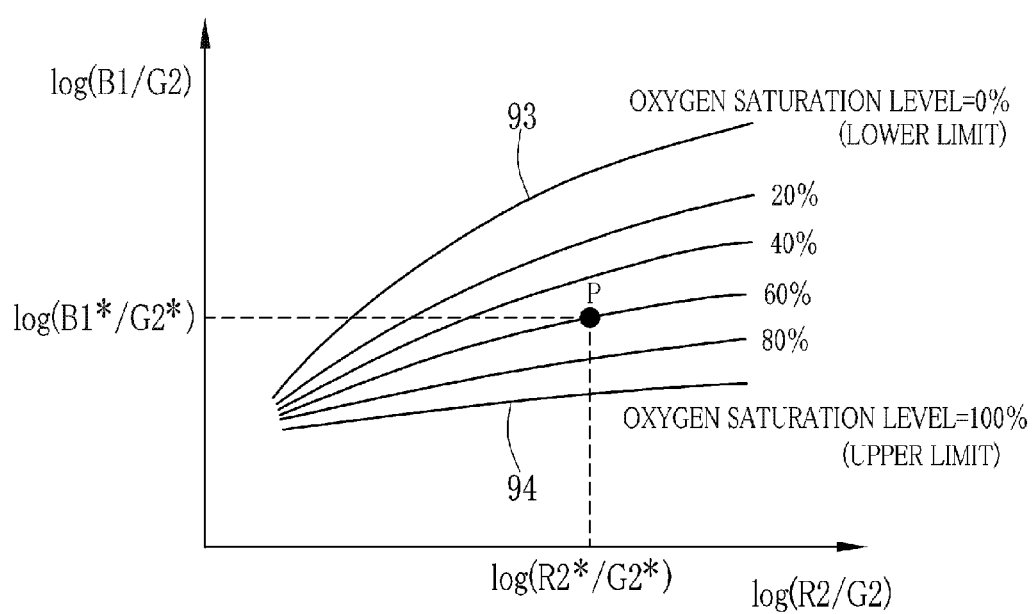
FIG. 11 is an explanatory view of a method for calculating the oxygen saturation level from the signal ratios in FIG. 8.

The oxygen saturation level calculator 86 calculates the oxygen saturation level of each pixel with the use of the correlations stored in the correlation memory 85 and the signal ratios B1/G2 and R2/G2 obtained by the signal ratio calculator 84. As shown in FIG. 11, a point P that corresponds to the signal ratios B1*/G2* and R2*/G2* obtained by the signal ratio calculator 84 is determined in the correlation stored in the correlation memory 85. When the point P is situated between a lower limit line 93 representing an oxygen saturation level of 0% and an upper limit line 94 representing an oxygen saturation level of 100%, the point P indicates the percentile of the oxygen saturation level. Taking FIG. 11 as an example, the point P is situated in a contour line of 60%, so the oxygen saturation level is 60%.

On the other hand, in a case where the point is out of the range between the lower limit line 93 and the upper limit line 94, when the point is situated above the lower limit line 93, the oxygen saturation level is determined to be 0%. When the point is situated below the upper limit line 94, the oxygen saturation level is determined to be 100%. Note that, in a case where the point is out of the range between the lower limit line 93 and the upper limit line 94, the oxygen saturation level of the pixel is judged to be unreliable and may not be displayed on the monitor 14.

The video image generator 88 produces the special video image (oxygen saturation video image) based on the oxygen saturation level obtained by the oxygen saturation level calculator 86. The produced special video image is displayed on the monitor 14. In the special video image, for example, the entire normal video image may be artificially colored with specific colors in accordance with the degree of the oxygen saturation level. In another case, only a hypoxic area, which has the oxygen saturation level lower than a predetermined value, may be artificially colored, while the other areas may be displayed with normal colors (colors used in the normal video image).

The still image processor 82 carries out freeze processing in which a video frame is stored in a still image memory 74a as a still image at the moment of pressing a freeze button 16b provided in the electronic endoscope 12. In the normal mode, out of the normal video image, one or more video frames are stored as normal still images in the still image memory 74a by the freeze processing.

In the special mode, on the other hand, the freeze processing is carried out only when a movement judging unit 82a judges that the movement M is a threshold value or less. In the freeze processing, out of video frames composing the special video image, one or more video frames are stored as special still images in the still image memory 74a. Only the video frames captured at the moment when the movement M is equal to or less than the threshold value are stored, as described above, so it is possible to store only the images that have no or little deviation. Note that, in a case where even if the freeze button 16a is pressed, no freeze processing is carried out because of the large movement M, the monitor 14 may display as such.

Figure 12:
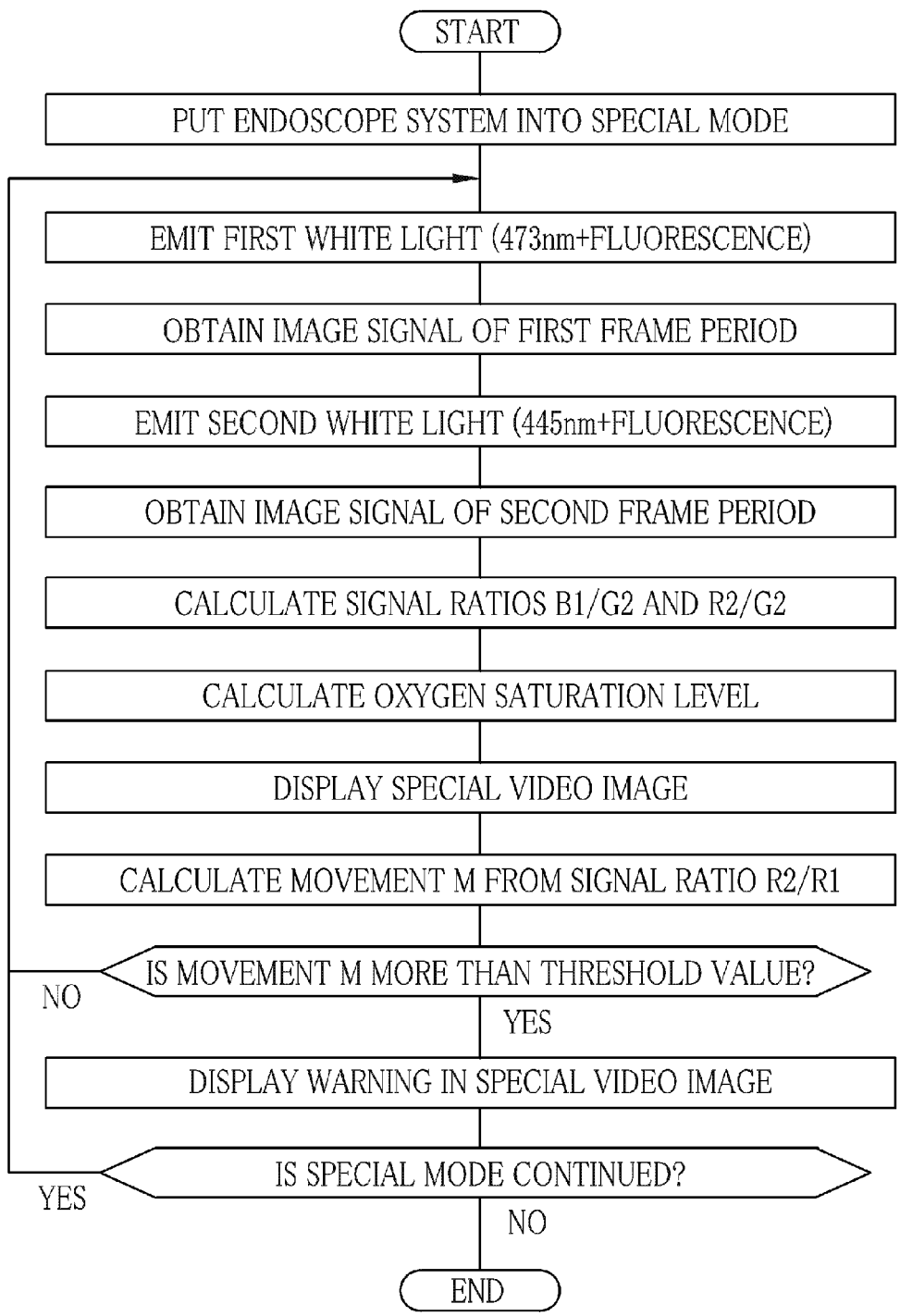
FIG. 12 is a flowchart of the special mode.

Next, the operation of the present invention will be described with referring to a flowchart of FIG. 12. When the endoscope system 10 is switched to the special mode by operation of the mode switch 21 provided in the electronic endoscope 12, the first white light is applied to the internal body portion. The image sensor 60 captures the reflected first white light to obtain the image signal of the first frame period. Thus, the first frame image including the blue signal B1, the green signal G1, and the red signal R1 is obtained.

After that, the second white light is applied to the internal body portion. The image sensor 60 captures the reflected second white light to obtain the image signal of the second frame period. Thus, the second frame image including the blue signal B2, the green signal G2, and the red signal R2 is obtained.

Then, the signal ratio calculator 84 calculates the signal ratios B1/G2 and R2/G2 of each and every pixel. The oxygen saturation level calculator 86 calculates the oxygen saturation level of each pixel, based on the correlation stored in the correlation memory 85 and the signal ratios B1/G2 and R2/G2. The special image is produced based on the calculated oxygen saturation level. By displaying the produced special images in a sequential manner, the special video image is displayed on the monitor 14.

Whenever the single video frame of the special image is produced, the signal ratio R2/R1 between the red signal R1 of the first frame image and the red signal R2 of the second frame image is calculated. When the movement M obtained by the signal ratio R2/R1 is more than the threshold value, the warning sign "!!", which indicates "there is a possibility of the occurrence of artifact", is put in the special video image. When the signal ratio R2/R1 is larger than the predetermined range S, the warning sign "HIGH StO$_2$" is put in the special video image to indicate that "a calculated oxygen saturation level is possibly higher than an actual value". On the other hand, when the signal ratio R2/R1 is smaller than the predetermined range S, the warning sign "LOW StO$_2$" is put in the special video image to indicate that "a calculated oxygen saturation level is possibly lower than an actual value". The above operation sequence is repeated as long as the endoscope system 10 stays in the special mode.

Figure 13:
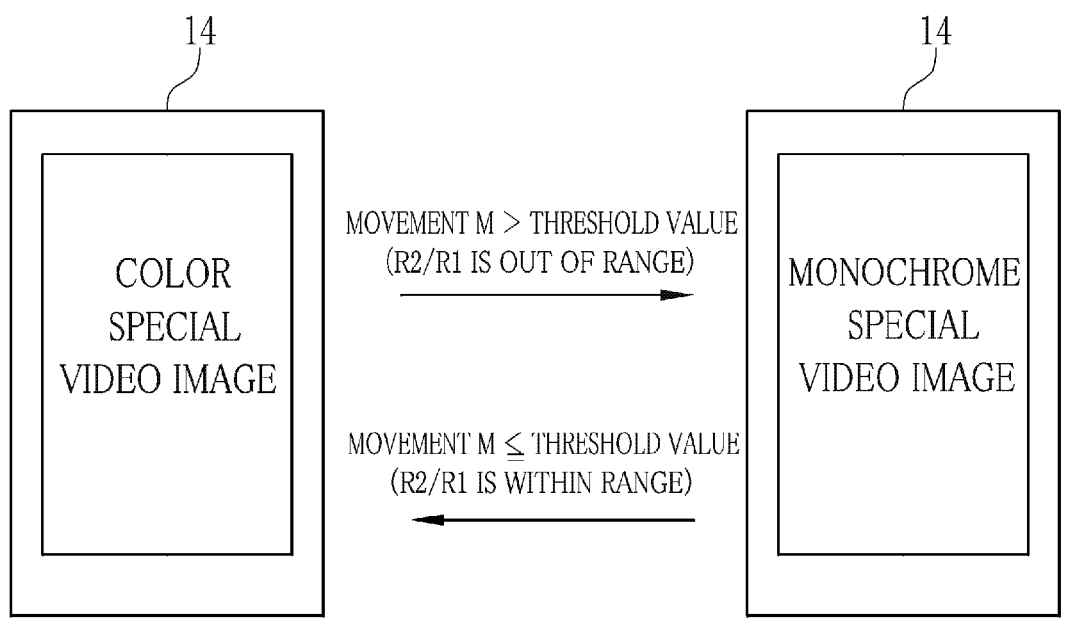
FIG. 13 is an explanatory view for explaining that how to display the special video image is switched depending on movement M.

In the above embodiment, when the movement M is more than the threshold value, the warning sign indicating "there is a possibility of the occurrence of artifact" is issued. Instead of or in addition to this, as shown in FIG. 13, the special video image may be displayed in monochrome in a case where the movement M is more than the threshold value or out of the predetermined range, while the special video image may be displayed in color in a case where the movement M is the threshold value or less or within the predetermined range.

In the above embodiment, the phosphor 50 is provided in the head assembly 19, but may be provided in the light source device 11. In this case, the phosphor 50 is disposed between the laser source LD1 (473 nm) and the optical fiber 24 and between the laser source LD2 (445 nm) and the optical fiber 25.

In the above embodiment, the oxygen saturation video image is used as an example of the special video image. However, the present invention is applicable to any image (NBI image and the like) that is composed of a plurality of frame images obtained by a sequential method, including a frame sequential method and a line sequential method.

In the above embodiment, the warning sign is put in the special video image, but another type of information such as text may be used as warning information. For example, text of "there is a possibility of the occurrence of artifact" may be displayed in the video image. To give a warning, a lamp provided on the monitor may be turned on, instead of displaying the warning sign or text in the video image.

Note that, the oxygen saturation level is imaged in this embodiment. However, an oxygenated hemoglobin index calculated by "blood volume (the sum of oxygenated hemoglobin and deoxygenated hemoglobin)×oxygen saturation level (%)" or a deoxygenated hemoglobin index calculated by "blood volume×(100−oxygen saturation level) (%)" may be imaged instead of or in addition to the oxygen saturation level.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
a lighting section for sequentially applying a plurality of types of illumination light having different wavelength bands to an internal body portion;
an image pickup section for sequentially capturing reflected light from said internal body portion to obtain a plurality of frames of image signals corresponding to said types of illumination light;
a video image generator for producing an endoscopic image of one video frame based on said plurality of frames of image signals, and sequentially outputting a plurality of produced endoscopic images to produce an endoscopic video image;
a monitor for displaying said endoscopic video image; and
a warning unit for issuing a warning, when a signal ratio between at least two of said image signals is out of a predetermined range.

2. The endoscope system according to claim 1, wherein
said lighting section emits first illumination light in a first frame period and second illumination light in a second frame period, and said first and second illumination light has same spectral distribution in a specific wavelength range;
said image pickup section obtains a first image signal in said first frame period and a second image signal in said second frame period, with use of a color image sensor having a specific pixel having a color filter for passing light in said specific wavelength range; and
when a signal ratio between a first signal component of said first image signal and a second signal component of said second image signal is out of a predetermined range, said warning unit issues said warning,
wherein said first signal component refers to a component of said first image signal outputted from said specific pixel, and said second signal component refers to a component of said second image signal outputted from said specific pixel.

3. The endoscope system according to claim 2, wherein
said first illumination light includes first blue light in a narrow wavelength band and first green to red light in a wide wavelength band, and said first green to red light is obtained by wavelength conversion of said first blue light using a wavelength conversion element;
said second illumination light includes second blue light in a narrow wavelength band and second green to red light in a wide wavelength band, and said second green to red light is obtained by said wavelength conversion of said second blue light using said wavelength conversion element, and a wavelength of said first blue light is different from a wavelength of said second blue light; and
said first and second illumination light has said same spectral distribution in a red wavelength range.

4. The endoscope system according to claim 3, wherein said first and second blue light is emitted from semiconductor light sources.

5. The endoscope system according to claim 1, wherein when said signal ratio is out of a first numerical range, said warning unit issues a first warning about a body motion of said internal body portion or a shake of an image sensor.

6. The endoscope system according to claim 1, wherein
said endoscopic video image is an oxygen saturation video image that images an oxygen saturation level of blood; and
when said signal ratio is out of a second numerical range, said warning unit issues a second warning about said oxygen saturation level.

7. The endoscope system according to claim 1, wherein said warning unit issues said warning by changing how to display said endoscopic video image on said monitor.

8. The endoscope system according to claim 1, wherein said warning unit issues said warning by displaying a warning sign on said monitor.

9. The endoscope system according to claim 8, wherein said warning sign is displayed on said monitor together with said endoscopic video image.

10. The endoscope system according to claim 1, further comprising a still image recording section for storing one or more video frames of said endoscopic images as still images in a still image memory, when said signal ratio is within said predetermined range.

11. A processor device of an endoscope system having a lighting section for sequentially applying a plurality of types of illumination light having different wavelength bands to an internal body portion, an image pickup section for sequentially capturing reflected light from said internal body portion to obtain a plurality of frames of image signals corresponding to said types of illumination light, and a monitor, said processor device comprising:

a video image generator for producing an endoscopic image of one video frame based on said plurality of frames of image signals, and sequentially outputting a plurality of produced endoscopic images to said monitor to produce an endoscopic video image; and a warning unit for issuing a warning, when a signal ratio between at least two of said image signals is out of a predetermined range.

12. A method for displaying an endoscopic video image comprising the steps of:

sequentially applying a plurality of types of illumination light having different wavelength bands to an internal body portion;

sequentially capturing reflected light from said internal body portion to obtain a plurality of frames of image signals corresponding to said types of illumination light;

producing an endoscopic image of one video frame based on said plurality of frames of image signals;

sequentially displaying on a monitor as an endoscopic video image a plurality of said endoscopic images produced by repetition of said applying step, said capturing step, and said producing step;

comparing a signal ratio between at least two of said image signals with a predetermined range; and issuing a warning, when said signal ratio is out of said predetermined range.

13. The method according to claim 12, wherein said warning is displayed on said monitor together with said endoscopic video image.

* * * * *